United States Patent [19]
Kantor et al.

[11] Patent Number: 4,877,016
[45] Date of Patent: Oct. 31, 1989

[54] VIDEO ENDOSCOPIC MICROSCOPE

[76] Inventors: Edward A. Kantor, 9872 Whitwell Dr., Beverly Hills, Calif. 90210; George Berci, 555 Levering Ave., #309, Los Angeles, Calif. 90024; Karl Storz, AM Schildrein 39, 7200 Tuttlingen, Fed. Rep. of Germany

[21] Appl. No.: 226,417

[22] Filed: Jul. 29, 1988

[51] Int. Cl.4 ............................ A61B 1/04; A61B 1/06
[52] U.S. Cl. ............................................. 128/6; 358/98
[58] Field of Search .......................... 128/4, 5, 6, 7, 11; 358/98

[56] References Cited

U.S. PATENT DOCUMENTS

| | | | |
|---|---|---|---|
| Re. 31,289 | 6/1983 | Moore et al. | 128/6 |
| 2,932,294 | 4/1960 | Fourestier et al. | 128/6 |
| 2,987,960 | 6/1961 | Sheldon | 128/6 X |
| 3,373,736 | 3/1968 | Fiore et al. | 128/6 |
| 3,496,931 | 2/1970 | Pilling | 128/6 |
| 3,592,199 | 7/1971 | Ostensen | 128/6 |
| 4,567,882 | 2/1986 | Heller | 128/11 |
| 4,714,075 | 12/1987 | Krauter | 128/4 |

Primary Examiner—William H. Grieb
Attorney, Agent, or Firm—Marvin H. Kleinberg

[57] ABSTRACT

An endoscope is provided with an integral optical element which includes a lens system and an objective lens that is recessed approximately 15 mm from the distal end of the endoscope. An integral illuminating element includes a fiber optic bundle that terminates at the distal end of the endoscope and illuminates the region of the distal end. The lens system terminated in a viewing port that is laterally displaced from the proximal end of the endoscope and which connects to a high resolution video camera that can display a magnified image on a high resolution video monitor, thus obviating the need for an unimpaired visual path from the proximal to the distal end of the endoscope. A lumen can be provided adjacent the lens system which brings a ventilating and clearing gas over the objective lens to keep the lens clear. The magnified video image can also be supplied to printers and recorders.

20 Claims, 3 Drawing Sheets

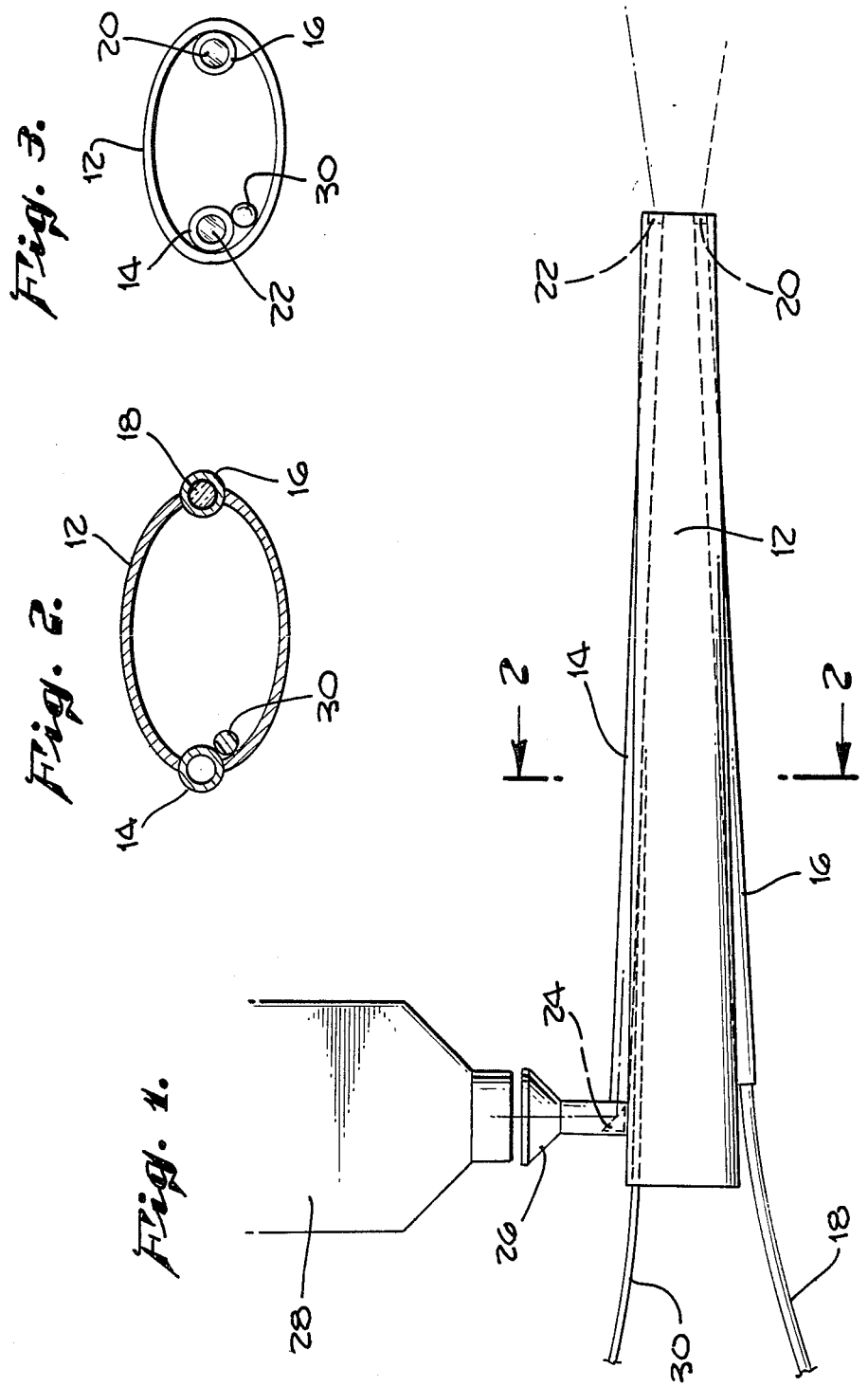

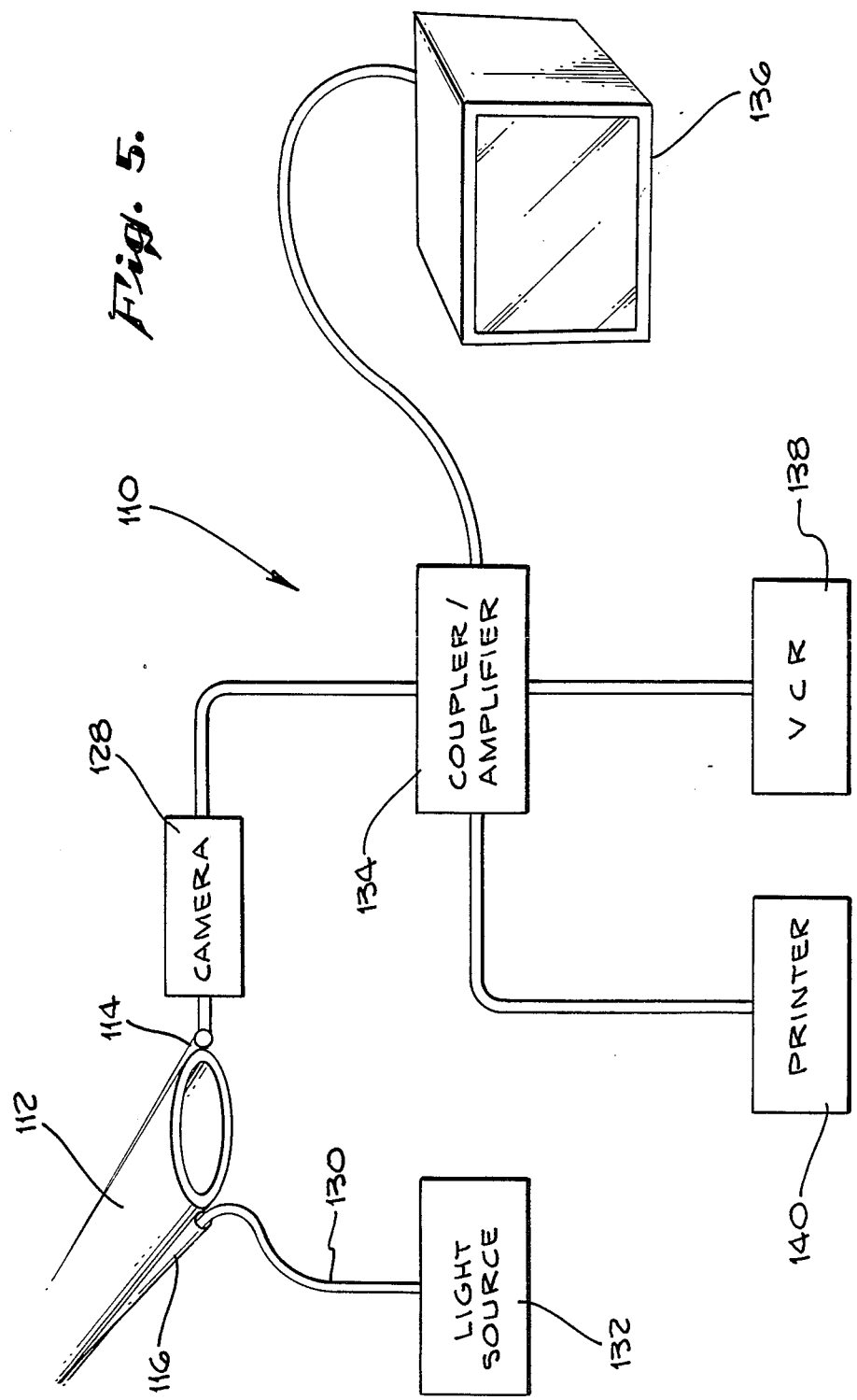

VIDEO ENDOSCOPIC MICROSCOPE

INTRODUCTION

The present invention relates to optical systems and, more particularly, to an improved system for visualizing objects within a surgical endoscopic field in aid of microsurgical procedures.

Physicians and especially surgeons have long had the need to see, in detail, the anatomical features upon which they operate during the course of a procedure. In many instances, the operating field is sufficiently exposed and accessible so that the naked eye is adequate for the work at hand. When, however, the objects in the field are too small to be easily seen with the naked eye, or the field is not at the surface, some form of instrumentation is necessary to permit a visualization of the working area.

For many years, optical instrument makers provided microscopes, both monocular and binocular, which permitted a surgeon to view the surgical field with a selected magnification. Such instruments tend to be large, bulky, and require either a wall or ceiling mounting or a large stand to support the optics without undue vibration. Moreover, such systems required careful alignment and focussing, especially if the depth of field was limited to a plane of approximately one millimeter thickness.

In many of these optical instruments, beamsplitters could be used to provide a second or more viewing stations. These would be utilized by assistants, students or could be used for archival purposes by mounting cameras or the like. Cameras could be utilized for still or motion picture photography, or, as in more modern systems, video cameras can be employed which are coupled to videotape machines or video monitors.

In a purely optical system, each time a beamsplitter is employed, the brightness of the transmitted image is reduced, thereby limiting the number of viewing stations by the extent to which the field can be illuminated. It is, of course, possible to use electronic light amplification techniques to the video system, enabling a record to be made under marginal viewing conditions.

Video cameras have taken a greater role in the surgical theater with the advent of lighter, smaller and higher resolution video cameras. Arthroscopes can be fitted with video cameras so that the surgeon can "see" what he is doing on a large screen, color video monitor. To some extent, the mere transmission of an image from the photosensitive transducer area of the video camera to the much larger screen of the monitor provides some degree of magnification with acceptable image resolution.

Endoscopes, however, have permitted some visualization of the field with optical paths that have utilized prisms and lenses or optical fibers. Usually such optical paths have either terminated in an eyepiece or in the objective plane of a conventional surgical microscope.

Conventional surgical microscopes have the several problems associated with large mass and weight, necessitating special supporting stands or mountings. Further, once the patient is readied, the microscope must be trained on the field of interest and focussed. If any photographs are taken, they will appear substantially "flat" and planar since only a fairly "thin" section is in focus at any given time and if a feature or artifact that is closer or farther from the focal plane is to be viewed, the focus of the microscope must be readjusted.

When the conventional microscope is used with an endoscope, (for example, a laryngoscope for exploring the vocal chords) the object distance is usually around 400 mm so that the microscope does not interfere with the insertion of instruments into the endoscope or with their manipulation. Moreover, the instruments themselves frequently occlude much of the available field of view. Even without an endoscope, dealing with an exposed surgical field still requires careful initial adjustment of the microscope and frequent refocussing if elements of interest are in a plane different from the focal plane.

If the endoscope is a laryngoscope, the patient must be anaesthetized and the laryngoscope inserted into the mouth and then past the tongue into the trachea. A binocular microscope with an integral light source is positioned approximately 400 mm from the tube and illuminates the field. In most cases, the field of view includes the opening of the laryngoscope into which instruments are inserted, the inner walls of the laryngoscope and the larynx or other organ of interest. Approximately 60% of the field of view is not of interest and is usually out of focus so as to visualize the larynx in focus.

The surgeon then must introduce whatever instruments he is to use into the laryngoscope in the area between the laryngoscope and the microscope. To a certain extent, the instruments will occlude the field of view and great care must be taken to position the instruments so that they can be seen, in focus, in the microscope eyepieces. Because the depth of field is so shallow, the microscope must be refocussed, each time a different plane is to be viewed. This is a great disadvantage if the object of interest extends for any distance in the axial direction.

The use of the conventional binocular microscope imposes its own special problems upon the surgeon who must remain more or less immobilized in order to view the field through the binocular eyepieces. Viewing through the small eyepieces also causes fatigue in the viewer, especially if the procedure is a long and difficult one. If an assistant wishes to follow the procedure, an optical beamsplitter can be employed with a second set of eyepieces, but at the cost of available light since each time a beam splitter is employed, the available light must be divided.

If one wishes to document the procedure, either through the use of a still camera or a motion picture or video camera, a beam splitter is required which reduces the illumination to both the primary operator and to the camera. Moreover, the optimum focus for the human viewer may not result in an optimum focus for the camera. To further complicate matters, the shallow depth of field results in much of the foreground and background of the image being out of focus.

The present invention is intended to alleviate many of the shortcomings of the conventional surgical microscope and to provide many benefits that are presently unavailable.

For the purposes of the present invention, the term "endoscope" is intended to include all of the specialized instruments which are introduced into the body of a patient and would include laryngoscopes, mediastinoscopes and rectoscopes, scopes, among others.

Some experimental work has been done with laryngoscopes wherein a special "telescope" was provided that was mounted on the inner wall of the laryngoscope.

In one example, a tube of 5 mm diameter was fitted with optical elements and fastened to a recess in a side wall. At the distal end, the telescope tube terminated approximately 15 mm from the end of the laryngoscope. The telescope was provided with an objective whose "view" was angled by approximately 6° with a viewing angle of approximately 60°, thereby permitting visualization of the entire area before the laryngoscope.

Near the proximal end of the laryngoscope, the telescope tube angled outwardly through the wall of the laryngoscope, terminating in an eyepiece or video camera objective that was positioned off of the axis of the laryngoscope. In a preferred embodiment, the angle is 90°, but other orientations are possible, depending upon how one would position the camera.

Illumination can be provided by a fiber optic bundle that parallels the telescope. Further, a miniature tube (outside diameter of 0.1 mm) can be used to flow oxygen or fresh air to the distal end of the telescope to act as a defogger. The effective aperture of the telescope is quite high, approximately f:100, which provides sufficient depth of field so that a substantial distance beyond the end of the laryngoscope is always in focus and the view to the operator and the camera can be considered three dimensional.

The key to the present invention is the use of a high resolution, miniaturized color video camera with a sensor area of approximately 6–7 mm diameter. An optical system brings the image of an area whose diameter is approximately 20 mm to the sensor element. The use of an all electronic system enables the use of a large screen, high resolution monitor to present the working area to the surgeon as well as to assistants and aides. Because the system is electronic, additional monitors can be placed in different locations for use by others in the surgical team or by students and spectators.

The electronic video signal can also drive video recorders, still cameras and/or printers which are capable of giving a "hard copy" record of any particular scene that is shown on the monitor for an archival record of the procedure without the need for additional illumination. Electronic image enhancers or light amplifiers can provide excellent images with the available light from the fiber optic illuminating system.

Further advantages and features of the present invention will be more fully apparent to those skilled in the art to which the invention pertains from the ensuing detailed description thereof, regarded in conjunction with the accompanying drawings wherein like reference numerals refer to like parts throughout and in which:

FIG. 1 is a bottom view of an improved video microscopic endoscope according to the present invention;

FIG. 2 is a section view of the endoscope of FIG. 1, taken along line 2—2 in the direction of the appended arrows;

FIG. 3 is an end view of the distal end of the endoscope of FIG. 1:

FIG. 5 is a block diagram illustrating one possible video setup including monitors and recording devices.

Figure 4:
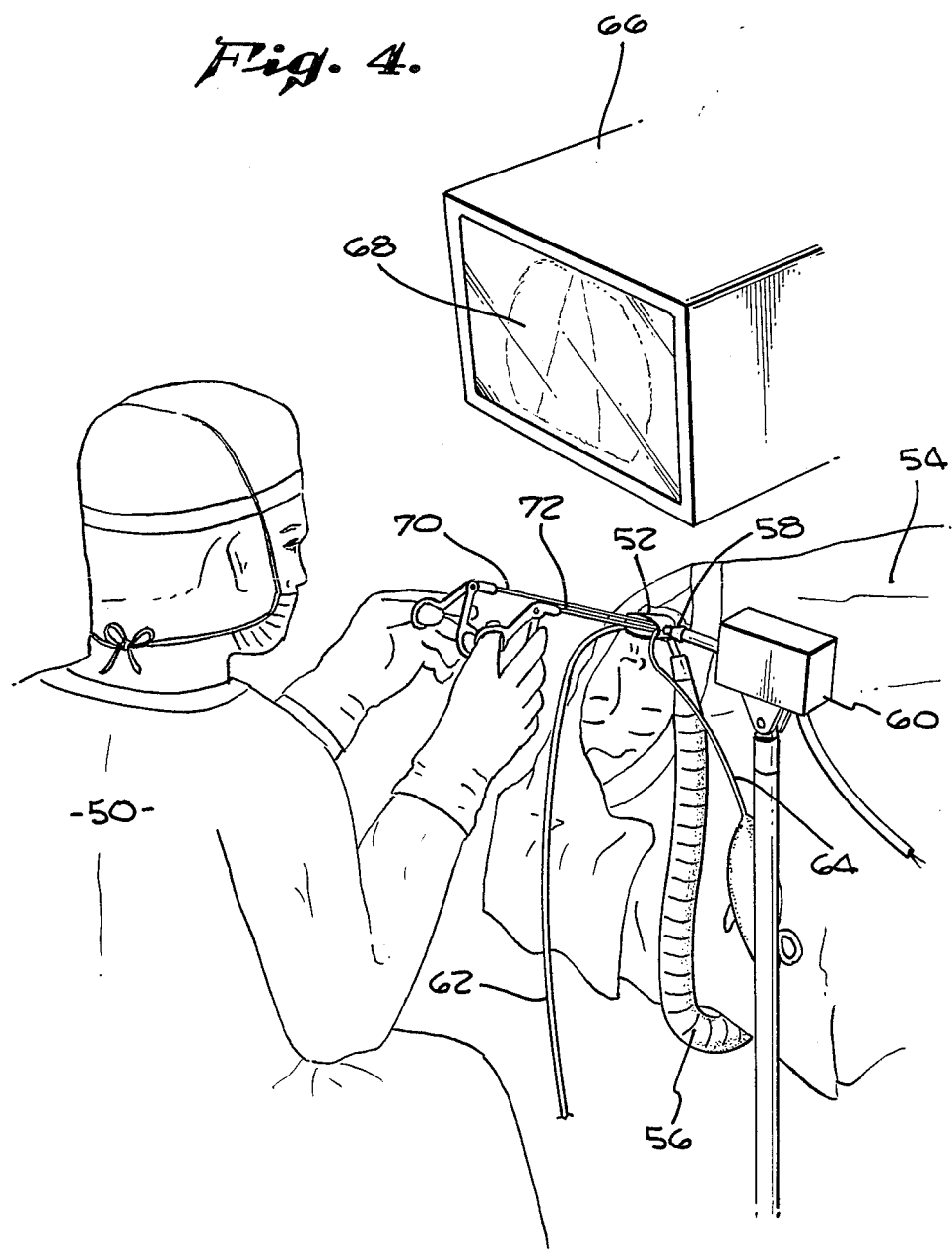
FIG. 4 is a side section view of the endoscope of the present invention employed as a laryngoscope, showing also the associated video camera and display equipment.

Turning first to FIG. 1, there is shown the improved video endoscopic microscope 10 of the present invention. As shown, there is a taper from the proximal to the distal end thereof. The endoscope tube 12 is provided with a first tubular channel 14 that extends along one side and which penetrates the side wall so that it is on the interior of the tube 12 at the distal end and recessed somewhat therefrom.

Similarly, on the opposite wall, a second tubular channel 16 extends along the side and penetrates to be on the interior at the distal end, as well. A fiber optic bundle 18 carries illuminating light to a lens 20 on the distal end of the second channel 16. The fiber optical bundle is coupled to a source of illumination (not shown).

The first channel 14 is fitted with optical elements and terminates in a scanning lens 22 at the distal end. The first channel 14 can then be considered a telescope or possibly a periscope. The optical elements include a combination of lenses which give both magnification and an extremely high aperture, approximately f:100. At the proximal end of the first channel 14 ia a prism 24 which bends the image to an optic coupler 26 which enables attachment of a video camera 28.

As seen in FIG. 1, the first and second channels 14, 16, are wholly without the endoscope 12 at the proximal end and are wholly within the endoscope 12 at the distal end. This can also be seen in connection with FIGS. 2 and 3, which are a sectional and end view, respectively, of the endoscope 12.

In FIG. 2, the first and second channels 14, 16 are shown partially within the endoscope 12 and in FIG. 3, the first and second channels 14, 16 are shown wholly within the endoscope 12. A lumen 30 within the endoscope 12 is coupled to a source of oxygen or other gaseous mixture. At its distal end, the lumen 30 directs the gaseous mixture over the lens 22 in the first channel 14 to keep the lens 22 clear of moisture or other visual obstructions.

Turning next to FIG. 4, there is shown a view of an operating theater in which the endoscope of the present invention is used as a laryngoscope. A surgeon 50 has placed a laryngoscope 52 in a patient 54. A catheter 56 parallels the laryngoscope 52 and supplies a breathing mixture to the lungs of the patient 54. A first, optical channel 58 is coupled to a video camera 60 and a second, illuminating channel 62 is coupled to a source of illumination (not shown). A lumen 64 is connected to a tube supplying an appropriate gaseous mixture at a velocity suitable to keep the lens at the distal end of the optical channel from fogging or being otherwise obscured.

A video monitor 66 is positioned at a height and location convenient to the surgeon 50 and presents an image 68 of the scene at the distal end of the laryngoscope 52 which, in this instance, would be image of the patient's larynx. By watching the monitor 66, the surgeon 50 can manipulate and operate various instruments 70, 72 which are inserted into the proximal end of the laryngoscope 52, the magnified image of which can be viewed.

Because of the magnification available through the optical system of the first channel 58, and the relative sizes of the monitor screen and the video transducer surface, the image presented to the surgeon 50 is far superior than was previously available using a surgical microscope. Not only can the entire larynx be visualized on the monitor, because of the high effective aperture, a substantial depth of field is available which means that the image is always in perfect focus.

Further, the microscopes of the prior art, because they were adjacent the surgeon, had to be focussed through the endoscope, the central area of which, therefore, of necessity, had to be kept relatively unobstructed, restricting the kinds and number of instruments available to the surgeon. In the present invention, the interior of the endoscope can be filled with instruments so long as the area in the region of the surgical field was visible to the distal lens of the first channel.

In preferred embodiments of the present invention, the first channel distal lens had a field of view of approximately 60° and, similarly, the second channel distal end had a lens that directed the illumination to the entire area of interest.

Finally, in FIG. 5, there is shown n block diagrammatic form, the various elements that make up a suitable system 110 employing the endoscope of the present invention. The endoscope 112, which has a first, optical channel 114 and a second, illuminating channel 116 is shown only in partial view. A video camera 128 is connected to the first channel 114 and a fiber bundle 130 couples the second channel 116 to a light source 132.

The video camera 128 is connected to a video amplifier 134 which drives a monitor 136, a recorder 138 and a printer 140 for a permanent record of successive events of a procedure. Because light amplification as well as signal amplification is possible in the video chain, many utilization devices can be employed without the loss of the image to the surgeon or any degradation of the quality of the image. Such cannot be said of the conventional surgical microscope.

What is claimed as new is:

1. An improved endoscope including an extended side wall having distal and proximal ends comprising in combination:
    a first tube having distal and proximal ends extending the length of the endoscope, said distal end being wholly within the endoscope and adjacent the side wall at the distal end thereof;
    optical system means within said first tube including a lens at said distal end for magnifying objects of interest, said optical system means being capable of viewing an area up to 25 mm with a depth of field in excess of 10 mm; and
    viewing means coupled to said first tube and extending laterally from the endoscope at the proximal end thereof to provide a viewing port remote from the interior of the endoscope;
    whereby a magnified image of an area of interest accessible to the distal end of the endoscope can be viewed from a location that is laterally displaced from the side wall of the endoscope.

2. The endoscope of claim 1, above, wherein said first tube is recessed from the distal end of the endoscope side wall by approximately 15 mm.

3. The endoscope of claim 2, above, wherein said lens has an offset of approximately 5°.

4. The endoscope of claim 2, above, wherein said lens has a field of view of approximately 60°.

5. The endoscope of claim 1, above, wherein said first tube proximal end is outside of the endoscope side wall at the proximal end thereof and passes through the side wall intermediate the ends.

6. The endoscope of claim 1, above, further including a second tube having distal and proximal ends, extending the length of the endoscope, said distal end being wholly within the endoscope, said second tube carrying optical fibers and being adapted to connect to a light source for illuminating the field visualized by said optical means.

7. The endoscope of claim 6, above, wherein said second tube proximal end is outside of the endoscope side wall at the proximal end thereof and passes through the side wall intermediate the ends.

8. The endoscope of claim 1, above, further including a lumen having distal and proximal ends, extending the length of the endoscope, said distal end opening within the endoscope adjacent said first tube distal end for ventilating and cleaning said lens, said lumen being adapted to connect to a source of ventilating gas.

9. The endoscope of claim 8, above, wherein said lumen is wholly within the endoscope.

10. The endoscope of claim 8, above, wherein said lumen is wholly without the indoscope but penetrates the side wall to the interior in the region of said first tube distal end.

11. An endoscope having a proximal end and a distal end for visualizing the surgical field to assist in microsurgical procedures comprising in combination:
    a. a light source within the endoscope for illuminating the field adjacent the distal end of the endoscope;
    b. a high resolution video camera having a sensitive image receiving area of from 7-10 mm in diameter;
    c. a high resolution video monitor coupled to said camera for displaying images impinging upon said image receiving area; and
    d. lens system means including a first tube integral with the endoscope, said lens system means having a field of view of an area ranging from 15 to 25 mm with a depth of field ranging from 10-20 mm;
    whereby magnified images of objects of interest adjacent the distal end of the endoscope can be displayed on said video monitor to aid in microsurgical procedures.

12. The endoscope of claim 11, above, wherein the endoscope includes a lumen having a distal end adjacent the distal end of said lens system means for ventilating and clearing the distal end of said lens system means.

13. The endoscope of claim 11, above, wherein the area of the displayed image at said sensitive image receiving area is approximately 7 mm.

14. The endoscope of claim 11, above, wherein said light source includes a fiber optic bundle within a second tube integral with the endoscope and having a distal end at the distal end of the endoscope for illuminating the area visualized by said lens system means.

15. The endoscope of claim 11, above, wherein said lens system means includes viewing means extending laterally from the endoscope and coupled to said video camera for applying a magnified image to said image receiving area.

16. The endoscope of claim 15, above, wherein said viewing means diverts images laterally through the wall of the endoscope near the proximal end thereof to provide a camera viewing port remote from the central opening of the endoscope.

17. The endoscope of claim 11, above, wherein said lens system means includes an objective lens at said first tube distal end adjacent the distal end of the endoscope.

18. The endoscope of claim 17, above, wherein said objective lens is recessed approximately 15 mm from the distal end of the endoscope.

19. The endoscope of claim 17, above, wherein said objective lens is offset by 5°.

20. The endoscope of claim 17, above, wherein said objective lens has a field of view of approximately 60°.

* * * * *